(12) United States Patent
Gold et al.

(10) Patent No.: US 11,054,368 B2
(45) Date of Patent: Jul. 6, 2021

(54) SYSTEM FOR DETECTION OF DISEASE IN PLANTS

(71) Applicant: Wisconsin Alumni Research Foundation, Madison, WI (US)

(72) Inventors: Kaitlin M. Gold, Madison, WI (US); Amanda J. Gevens, McFarland, WI (US); Philip A. Townsend, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 12 days.

(21) Appl. No.: 16/251,415

(22) Filed: Jan. 18, 2019

(65) Prior Publication Data

US 2019/0219499 A1    Jul. 18, 2019

Related U.S. Application Data

(60) Provisional application No. 62/618,917, filed on Jan. 18, 2018.

(51) Int. Cl.
*G01N 21/3563*    (2014.01)
*G01J 3/42*    (2006.01)
(Continued)

(52) U.S. Cl.
CPC ....... *G01N 21/3563* (2013.01); *A01B 79/005* (2013.01); *A01G 7/00* (2013.01);
(Continued)

(58) Field of Classification Search
CPC .... G01J 3/42; G01J 3/2823; G01N 2021/359; G01N 2021/635; G01N 2021/3563;
(Continued)

(56) References Cited

U.S. PATENT DOCUMENTS

| 7,271,386 B2* | 9/2007 | Lawrence | G01N 21/3563 250/339.11 |
| 8,781,174 B2* | 7/2014 | Tseng | G06K 9/00 348/135 |
| 2016/0216245 A1* | 7/2016 | Sutton | G06K 9/00664 |

FOREIGN PATENT DOCUMENTS

KR    101619031 B1    5/2016

OTHER PUBLICATIONS

Machado, et al. (White Mold Detection in Common Beans through Leaf Reflectance Spectroscopy), pp. 1117-1126. (Year: 2015).*

(Continued)

*Primary Examiner* — Daniel G Mariam
(74) *Attorney, Agent, or Firm* — Boyle Fredrickson, S.C.

(57) ABSTRACT

The present inventors have recognized that various diseases in plants, such as *Phytophthora infestans* (late blight) and *Alternaria solani* (early blight), and/or various stages of such diseases in plants, can be reliably detected by applying measurements from electromagnetic reflections detected from a plant in a model to produce an output indicating a probability of the disease and/or stage. In one aspect, coefficients can be applied to each measurement at each wavelength to emphasize identification of a given disease or stage. In another aspect, an imager can capture images comprising spectral pixels in which each pixel comprises measurements from the electromagnetic reflections for application in a model to identify a given disease or stage.

18 Claims, 16 Drawing Sheets

(51) Int. Cl.
| | |
|---|---|
| G06T 7/00 | (2017.01) |
| G01J 3/28 | (2006.01) |
| A01B 79/00 | (2006.01) |
| A01G 7/00 | (2006.01) |
| G01N 21/359 | (2014.01) |
| G01N 21/84 | (2006.01) |
| G01N 21/63 | (2006.01) |
| G01N 33/00 | (2006.01) |

(52) U.S. Cl.
CPC .............. *G01J 3/2823* (2013.01); *G01J 3/42* (2013.01); *G01N 21/359* (2013.01); *G06T 7/0002* (2013.01); *G01N 33/0098* (2013.01); *G01N 2021/635* (2013.01); *G01N 2021/8466* (2013.01)

(58) Field of Classification Search
CPC ........ G01N 2021/8466; G01N 33/0098; G06T 7/0002; A01B 79/005; A01G 7/00
USPC .......................................................... 382/110
See application file for complete search history.

(56) References Cited

OTHER PUBLICATIONS

Abrahamian, et al. (Gene Expression and Silencing Studies in Phytophthora infestans Reveal Infection-Specific Nutrient Transporters and a Role for the Nitrate Reductase Pathway in Plant Pathogenesis), pp. 1-30. (Year: 2016).*
Huang, et al. (New Optimized Spectral Indices for Identifying and Monitoring Winter Wheat Diseases), pp. 2516-2524. (Year: 2014).*
Abu-Nada, Y.; "Temporal dynamics of pathogenesis-related metabolites and their plausible pathways of induction in potato leaves following inoculation with Phytophthora infestans"; research paper; May 15, 2007; 17 pages; Eur J Planto Pathol (2007).
Agrios, George N.; "Plant Pathology"; textbook; Jul. 2004; 24 pages; Elsevier Academic Press.
Avis, T.J.; "Integrated management of potato silver scurf (*Helminthosporium solani*)"; research paper; May 15, 2010; 11 pages; Can. J. Plant Pathol, (2010), 32(3).
Baranowski, Piotr; "Hyperspectral and Thermal Imaging of Oilseed Rape (*Brassica napus*) Response to Fungal Species of the Genus Alternaria"; research paper; Mar. 31, 2015; 19 pages; PLOS ONE.
Bauriegel, E.; "Early detection of Fusarium infection in wheat using hyper-spectral imaging"; research paper; Dec. 10, 2010; 9 pages; Computers and Electronics in Agriculture 75 (2011).
Bravo, Cedric; "Early Disease Detection in Wheat Fields Using Spectral Reflectance"; research paper; Nov. 19, 2002; 9 pages; Biosystems Engineering (2003) 84(2).
Carter, Gregory A.; "Leaf Optical Properties in Higher Plants: Linking Spectral Characteristics To Stress And Chlorophyll Concentration"; journal; 2001; 8 pages; American Journal of Botany 88(4).
Cavender-Bares, Jeannine; "Associations of Leaf Spectra with Genetic and Phylogenetic Variation in Oak: Prospects for Remote Detection of Biodiversity"; research paper; Mar. 9, 2016; 17 pages; Remote Sens. 8.
Chen, Sheng; "Sparse Modeling Using Orthogonal Forward Regression With PRESS Statistic and Regularization"; research paper; Apr. 2, 2004; 14 pages; IEE Transactions on Systems, Man, and Cybernetics—Part B: Cybernetics vol. 34, No. 2.
Chen, X.; "Detecting infestation of take-all disease in wheat using Landsat Thematic Mapper imagery"; research paper; Nov. 2007; 7 pages; International Journal of Remote Sensing; vol. 28, Nos. 21-22.
Chevallier, Sylvie; "Application of PLS-DA in multivariate image analysis"; research paper; Nov. 21, 2006; 9 pages; Journal of Chemometrics 20.
Daines, G.; "Phenotypic Characterization of Recent Clonal Lineages of Phytophthora infestans in the United States"; research paper; 9 pages; Jan. 7, 2013; The American Phytopathological Society; Plant Disease vol. 97, No. 7.
Del Fiore, A.; "Early detection of toxigenic fungi on maize by hyperspectral imaging analysis"; research paper; 8 pages; Aug. 3, 2010; International Journal of Food Microbiology 144.
Delalieux, Stephanie; "Detection of biotic stress (*Venturia inaeualis*) in apple trees using hyperspectral data; Non-parametric statistical approaches and physiological implications"; research paper; 14 pages; Feb. 22, 2007; European Journal of Agronomy.
Deller, Steve; "Economic Impact of Specialty Crop Production And Processing In Wisconsin"; research paper; 7 pages; Jul. 2016; Wisconsin's Annual Potato Meeting.
Dixon, Philip; "Vegan, a package of R functions for community ecology"; research paper; 4 pages; Oct. 9, 2003; Journal of Vegetation Science 14.
Dou, Daolong; "RXLR-Mediated Entry of Phytophthora sojae Effector Avr1b into Soybean Cells Does Not Require Pathogen-Encoded Machinery"; research paper; 18 pages; Jul. 2008; The Plant Cell vol. 20.
Du, Qian; "Citrus Pest Stress Monitoring Using Airborne Hyperspectral Imagery"; research paper; 4 pages; 2004; IEEE.
Eriksson, Lennart; "On the selection of the training set in environmental QSAR analysis when compounds are clustered"; research paper; 18 pages; Mar. 4, 2000; J. Chemometrics 14.
Errampalli, D.; "Emergence of silver scurf (*Helminthosporium solani*) as an economically important disease of potato"; research paper; 13 pages; 2001; Plant Pathology 50.
Fairchild, Katie L.; "Assessing fungicide resistance in populations of Alternaria in Idaho potato fields"; research paper; 9 pages; Mar. 11, 2013; Crop Protection 49.
Wu, D.; "Early Detection of Botrytis Cinerea on Eggplant Leaves Based on Visible and Near-Infrared Spectroscopy"; research paper; 8 pages; 2008; American Society of Agricultural and Biological Engineers 51.
Flinn, P.C.; "Near infrared analysis of the fodder shrub tagasaste (*Chamaecytisus proliferus*) for nutritive value and anti-nutritive factors"; research paper; 5 pages; 1996.
Franke, Jonas; "Multi-temporal wheat disease detection by multi-spectral remote sensing"; research paper; 12 pages; Jun. 24, 2007; Precision Agric 8.
Mahlein A.-K., Rumpf T., Welke P., Dehne H.-W., Plumer L., Steiner U., Oerke E.-C.; "Development of spectral indices for detecting and identifying plant diseases", Remote Sensing of Environment, vol. 128, Dec. 31, 2013 (Dec. 31, 2013), pp. 21-30, XP002791530, ISSN: 1879-0704, DOI: 10.1016/j.rse.2012.09.019 the whole document.
International Search Report and Written Opinion dated Jun. 12, 2019.

* cited by examiner

SYSTEM FOR DETECTION OF DISEASE IN PLANTS

CROSS-REFERENCE TO RELATED APPLICATION(S)

This application claims priority to U.S. Provisional Patent Application No. 62/618,917, entitled "System for Detection of Disease in Plants," filed on Jan. 18, 2018, which is herein incorporated by reference.

STATEMENT REGARDING FEDERALLY SPONSORED RESEARCH OR DEVELOPMENT

This invention was made with government support under 15SCBGW10054 and 16SCBGWI0017 awarded by the USDA Agricultural Marketing Service. The government has certain rights in the invention.

FIELD OF THE INVENTION

The present invention is directed to the field of detection of disease in plants, and more particularly, to a system for detection of disease in plants using a spectrometer configured to detect a spectrum of electromagnetic radiation reflected from a plant at multiple wavelengths.

BACKGROUND

Late blight of tomato and potato is a disease in plants caused by the hemibiotrophic oomycete pathogen *Phytophthora infestans* (*P. infestans*). Late blight was believed to be a major culprit in the 1840's European, the 1845 Irish and the 1846 Highland potato famines. The pathogen is favored by moist, cool environments, with sporulation optimal at about 12-18° C. in water-saturated or nearly saturated environments, and zoospore production favored at temperatures below about 15° C. Lesion growth rates are typically optimal at a slightly warmer temperature range of about 20 to 24° C.

Late blight continues to be one of the most challenging diseases to sustainably and proactively manage in modern agriculture. Significant resources are spent on *P. infestans* control every year, despite annual losses in significant numbers continuing to occur. It is therefore desirable to provide an advanced field-based system for detection of late blight that can reliably identify infection before the onset of visual symptoms. Such a system could improve management of crops by greatly reducing disease potential and spread, thereby potentially saving significant time and resources and reducing food and seed loss.

SUMMARY

The present inventors have recognized that various diseases in plants, such as *Phytophthora infestans* (late blight) and *Alternaria solani* (early blight), and/or various stages of such diseases in plants, can be reliably detected by applying measurements from electromagnetic reflections detected from a plant in a model to produce an output indicating a probability of the disease and/or stage. In one aspect, coefficients can be applied to each measurement at each wavelength to emphasize identification of a given disease or stage. In another aspect, an imager can capture images comprising spectral pixels in which each pixel comprises measurements from the electromagnetic reflections for application in a model to identify a given disease or stage.

In one aspect, the present invention relates to a system or method for using infrared reflectance of leaves to determine whether a plant is infected with *P. infestans*, before visual symptoms appear. The inventors measured continuous visible to shortwave infrared reflectance (400-2500 nanometers) on leaves of plants using a portable spectrometer at 12-24 hour intervals after inoculation of the plants, coinciding with different phases of *P. infestans*' life cycle, including: early infection (which could occur, for example, at about 24 hours post inoculation); biotrophic growth (which could occur, for example, at about 36-60 hours post inoculation); transition to necrotrophy (which could occur, for example, at about 84 hours post inoculation); necrotrophy (which could occur, for example, at about 108 hours post inoculation); and sporulation (which could occur, for example, at about 132 hours post inoculation). As the progression of infection over time may be affected by the aggressiveness of an isolate and conductivity of the environment, the present invention analyzes data according to infection stage and not just time.

The inventors calculated Normalized Differential Spectral Index (NDSI) values, identified NDSI values and wavelengths most correlated with the different stages of infection, and executed logistic and machine learning-based regressions to identify NDSI values whose changes may be most indicative of infection status. Accordingly, the inventors have identified distinctive NDSI bandwidth patterns that can be used to accurately determine infection at all stages of *P. infestans* infection, including before the appearance of visual symptoms. The aforementioned NDSI values can be applied across time points in a predictive mode to provide a hyperspectral reflectance and imaging system that can be used via direct contact with plants and/or via attachment vehicles such as tractors or drones. This can advantageously provide rapid, early detection of late blight in real-time In one aspect, for each stage of the *P. infestans* infection cycle, a predetermined set of NDSI values can be used in a model providing a multivariate regression to classify plants as likely infected and likely not infected. Models for each of the stages can be combined into a single algorithm that is run sequentially. Accordingly, each stage of the infection cycle which induces a different physical, physiological, and/or biochemical response from a plant, thereby causing wavelength reflectance to change, can be classified.

Specifically then, one aspect of the present invention can provide a system for detection of disease in plants, including: a spectrometer configured to detect a spectrum of electromagnetic radiation reflected from a plant at multiple wavelengths, the spectrum including reflection measurements corresponding to wavelengths; and a processor executing a program stored in a non-transient medium to apply the reflection measurements as variables in a model configured to indicate a likelihood of presence of a disease in the plant.

Another aspect of the present invention can provide a system for detection of disease in plants, including: an imager configured to a capture an image including multiple spectral pixels, each spectral pixel corresponding to a spectrum of electromagnetic radiation reflected at v wavelengths, the spectrum including reflection measurements corresponding to wavelengths; and a processor executing a program stored in a non-transient medium to apply reflection measurements at each spectral pixel as variables in a model configured to indicate a likelihood of presence of a disease of a plant at the spectral pixel.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

FIG. 7 is a diagram of an alternative system for detection of disease in plants in accordance with an aspect of the invention;

FIG. 8 is a process for detection of disease in plants in accordance with an aspect of the invention;

FIG. 9 is an exemplar plot of waveforms in a spectrum comparing a healthy plant to a plant inoculated with *P. infestans* at an early infection stage of infection;

FIG. 10 is an exemplar plot of waveforms in a spectrum comparing a healthy plant to a plant inoculated with *P. infestans* at a biotrophic growth stage of infection;

FIG. 11 is an exemplar plot of waveforms in a spectrum comparing a healthy plant to a plant inoculated with *P. infestans* at a necrotrophic lesion formation stage of infection;

FIG. 12 is an exemplar plot of waveforms in a spectrum comparing a healthy plant to a plant inoculated with *P. infestans* at a sporulation stage of infection;

FIG. 13 is a diagram illustrating generation of a model in accordance with an aspect of the invention;

FIG. 14 is a diagram illustrating an application of reflection measurements as variables in a model in accordance with an aspect of the invention;

FIG. 15 is a diagram illustrating an image comprising spectral pixels in accordance with an aspect of the invention; and FIG. 16 is a diagram illustrating an overhead vehicle capturing an image comprising spectral pixels in accordance with an aspect of the invention.

DETAILED DESCRIPTION

Referring now to FIG. 1, a diagram of a system 10 for detection of disease in plants is provided in accordance with an aspect of the invention. The system 10 can include a control system 12 in communication with a controllable light source 14, a spectrometer 16 and/or an I/O interface 18. The control system 12 can include a processor 20 configured to execute a program 22 stored in a non-transient medium 24 to control operation of the light source 14 and/or the spectrometer 16. The processor 20 can also execute to communicate with a user through the I/O interface 18 to receive commands and/or display results as described herein. The I/O interface 18 could include a keyboard and/or monitor connected to the control system 12, and in one aspect, could be implemented by a remote monitoring device, such as a smartphone or tablet.

Under control of the system 12, the light source 14 can project electromagnetic radiation over a continuous spectrum from a radiating portion 15, preferably including visible and infrared spectrums, at various distances and/or angles onto a plant 30, such as an exposed leaf under study. In alternative aspects, ambient lighting and/or other electromagnetic radiation sources could be used. Also, under control of the system 12, the spectrometer 16, through a sensor 26, which could include a lens, in turn, can detect a continuous spectrum of electromagnetic radiation at various distances and/or angles as reflected from the plant 30. In particular, the spectrometer 16 can detect the continuous spectrum of electromagnetic radiation as reflection measurements between lower and upper wavelengths, preferably between at least a lower (longer) wavelength of about 400 nanometers and an upper (shorter) wavelength of about 2500 nanometers.

In one arrangement, the system 10 can be configured as part of portable device carried by a user. In such an arrangement, the sensor 26 and the radiating portion 15 could be integrated into a single handheld contact probe for local testing and monitoring. In another arrangement, the system 10 can be attached to an aerial vehicle, such as a drone, for monitoring larger areas of an agricultural field. In yet another arrangement, the system 10 can be attached to a ground vehicle, such a tractor or agricultural implement, to interface with a user in a cab, for real-time monitoring of plant conditions during field operations.

With additional reference to FIG. 2, as full portions 32 of electromagnetic radiation projected from the light source 14 come into contact with the plant 30, the full portions 32 are typically divided into reflected portions 34, absorbed portions 36 and transmitted portions 38. The reflected portions 34 are typically further divided into surface reflected portions 34*a*, which reflect from the plant 30 without penetrating the surface, and internally reflected portions 34*b*, which penetrate the surface of the plant 30 and reflect from interior structures 40. The absorbed portions 36 most often constitute radiation in the red and blue regions of the visible light spectrum, among other radiation, that is absorbed by chlorophyll during photosynthesis. The transmitted portions 38 constitute radiation at particular wavelengths which are neither reflected nor absorbed by the plant 30.

The present inventors have recognized that various stages of an infection cycle of a disease can induce a different physical, physiological, and/or biochemical response from a plant, thereby causing wavelength reflectance to change. For example, a first portion 42 of the plant 30 not affected by disease reflects the reflected portions 34 in different ways at select wavelengths than a second portion 44 of the plant 30 that is affected by disease. Such reflected portions 34 can therefore be characterized to determine healthy versus diseased plants, and moreover, states of progression of diseased plants, such as early infection, biotrophic growth, transition to necrotrophy, necrotrophic lesion formation, sporulation, and/or disease-induced leaf death, for *Phytophthora infestans* (*P. infestans*) in potato or tomato.

Figure 1:
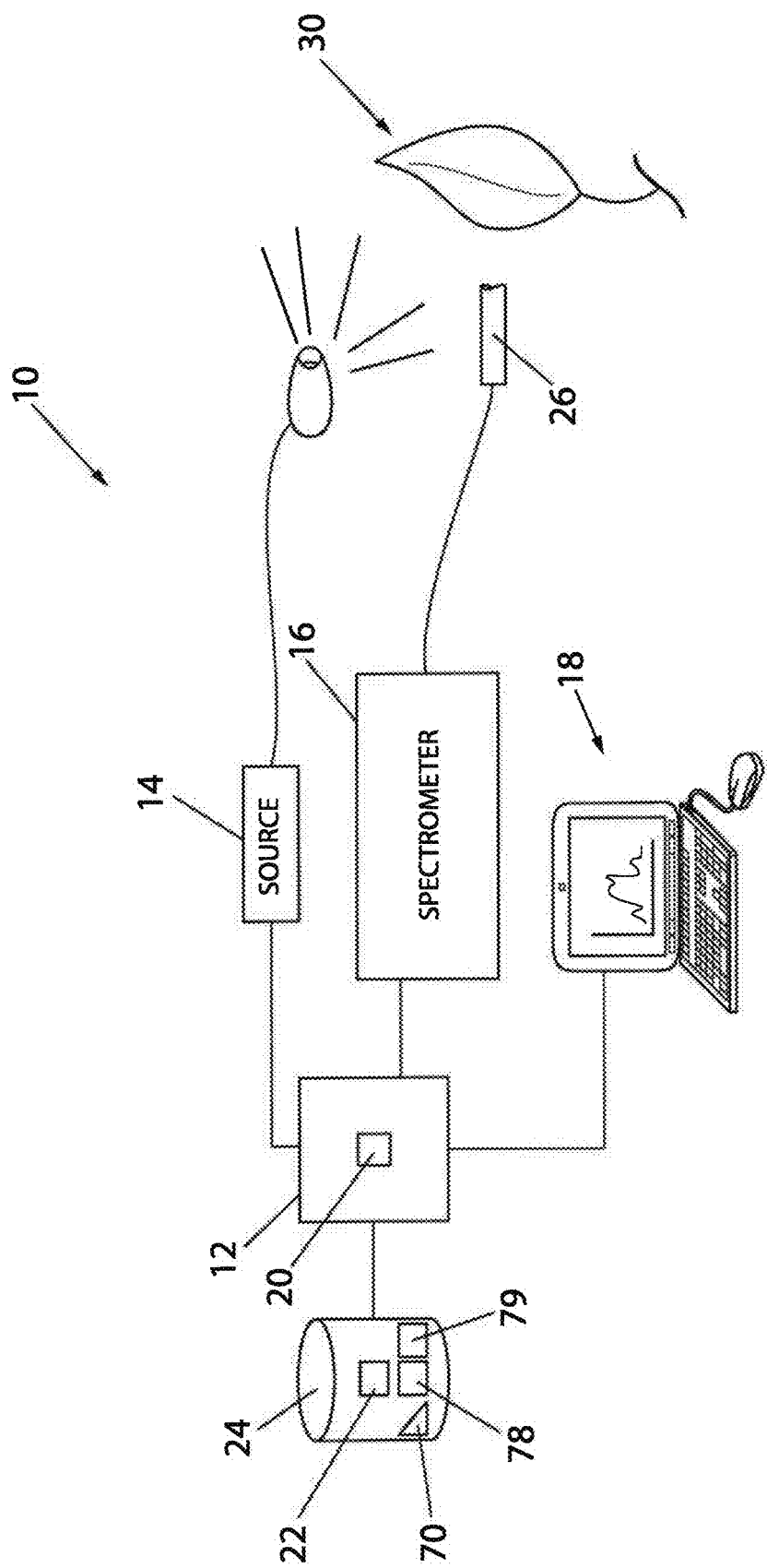
FIG. 1 is a diagram of a system for detection of disease in plants in accordance with an aspect of the invention.
Figure 2:
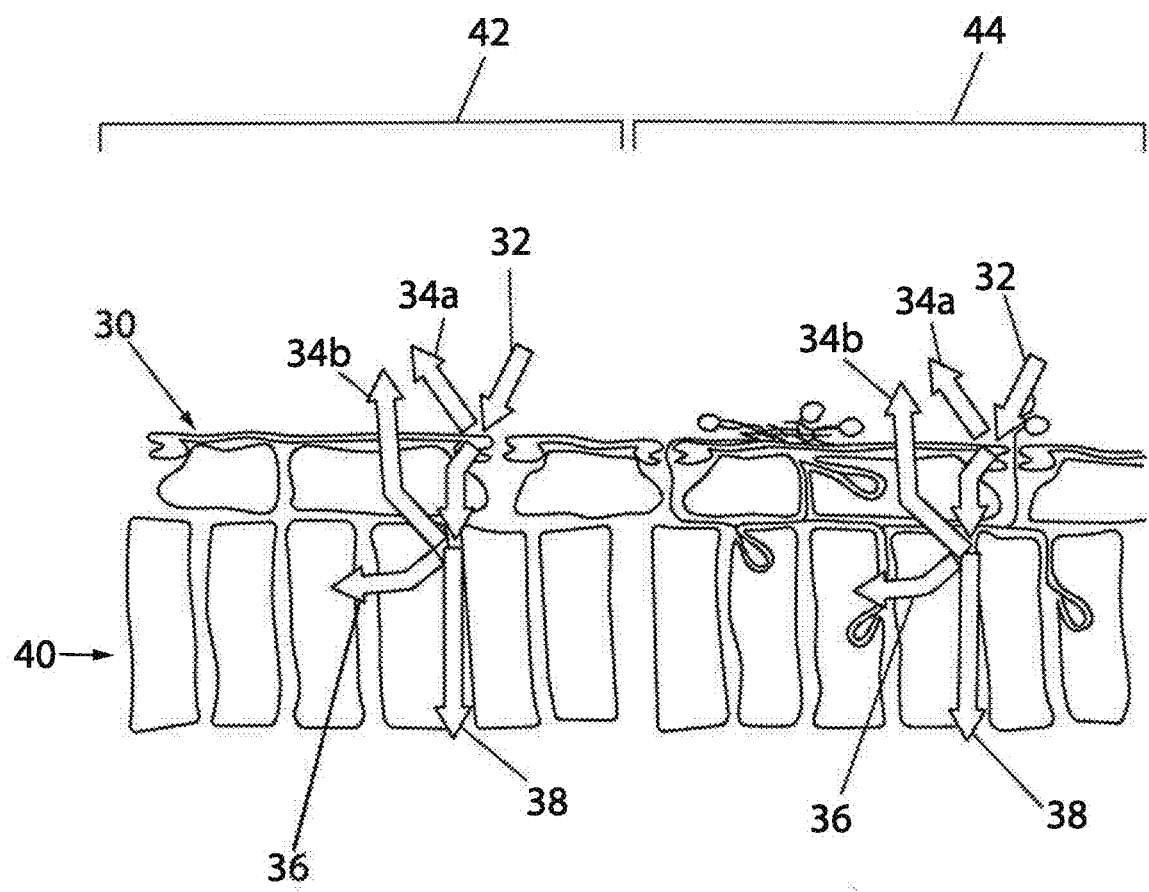
FIG. 2 is a diagram of an exemplar plant structure reflecting a spectrum of electromagnetic radiation in the system of FIG. 1.
Figure 3:
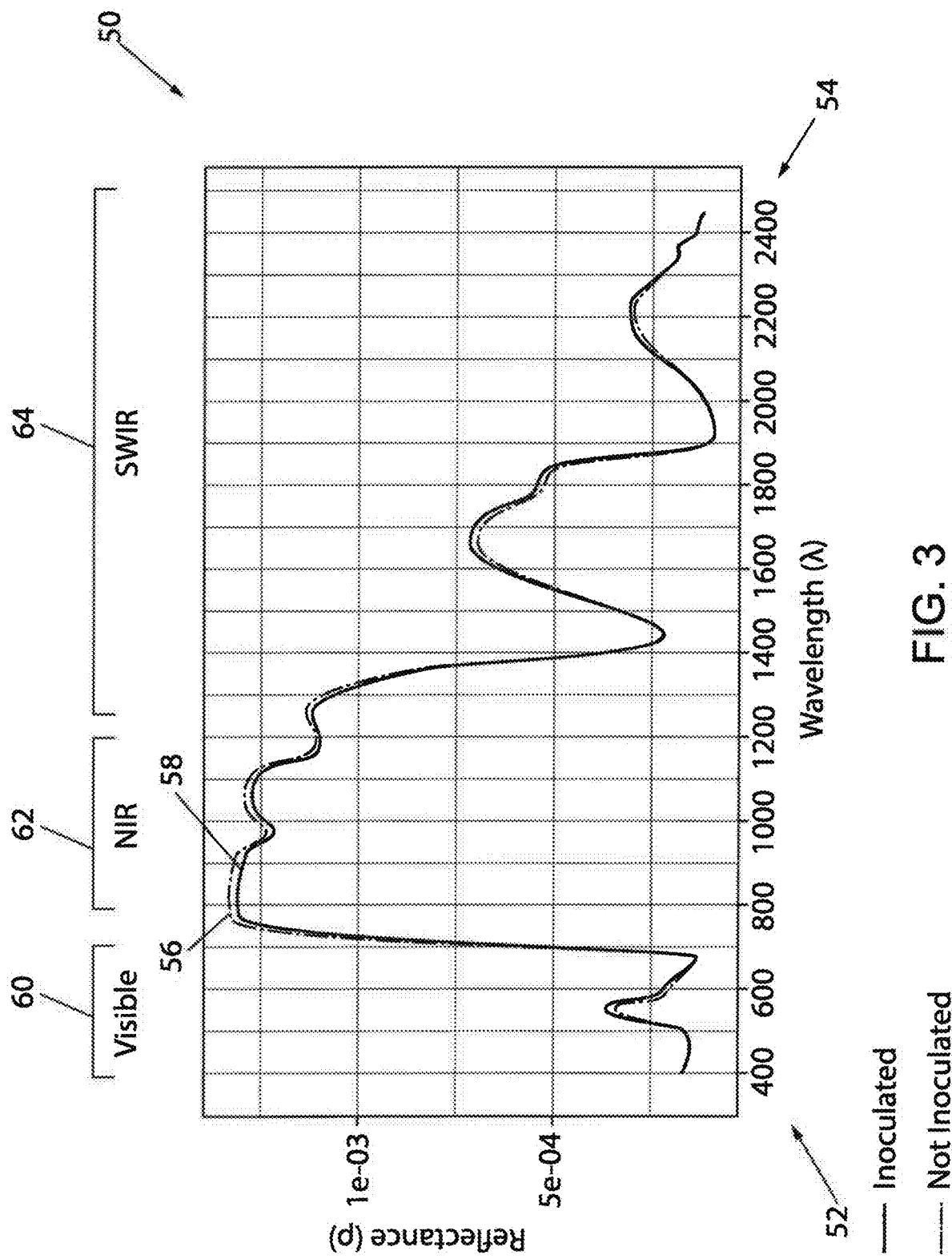
FIG. 3 is an exemplar plot of waveforms in a spectrum, including for a plant inoculated with a disease and a plant not inoculated with the disease, showing reflections from the plants by varying amounts across the spectrum of electromagnetic radiation indicated by wavelengths.
Figure 4:
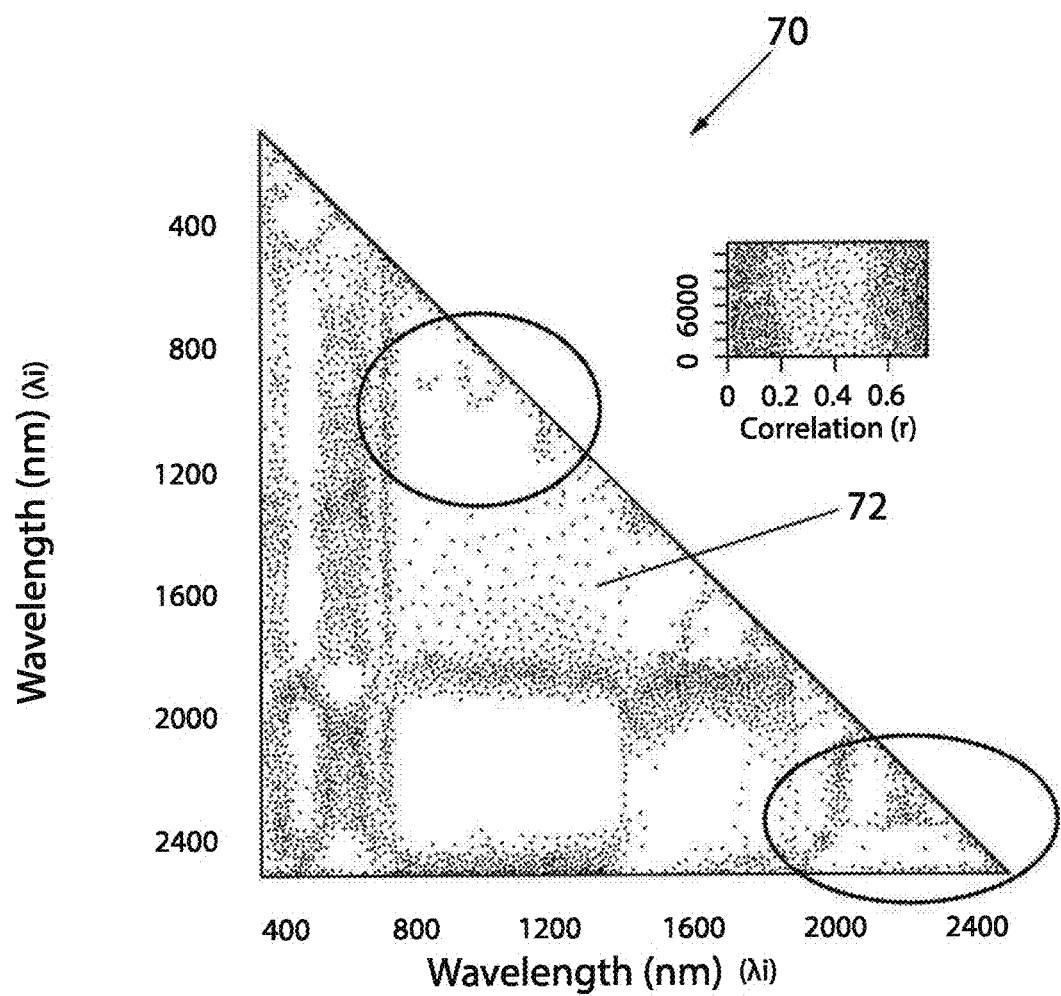
FIG. 4 is an exemplar plot of spectral values in a "heat map," which could be Normalized Differential Spectral Index (NDSI) values, calculated from reflections from a plant.

With additional reference to FIG. 3, an exemplar plot of waveforms 50 illustrates reflections (ρ) by varying amounts with respect to a spectrum of electromagnetic radiation at differing wavelengths (λ) between a lower wavelength 52 and an upper wavelength 54 in accordance with an aspect of the invention. Such waveforms 50 could be detected by the spectrometer 16, displayed to the I/O interface 18 and/or used for calculations by the processor 20 as described herein. The waveforms 50 include, by way of example, a non-inoculated waveform 56 for a plant not affected by disease ("Not Inoculated"), which could include only the first portion 42 of the plant 30, and an inoculated waveform 58 for a plant that is affected by disease ("Inoculated"), such could include the second portion 44 of the plant 30. In one aspect, such waveforms could be detected continuously between lower wavelengths of about 400 nanometers to upper wavelengths of about 2500 nanometers. The spectrum could therefore preferably include a visible spectrum 60 (VIS), between 400 and 700 nanometers, and an infrared (IR) spectrum, between 700 and 2500 nanometers. Accordingly, the IR spectrum would also include a near-infrared (NIR) division 62, approximately between 800 and 1200 nanometers, and a short-wavelength infrared (SWIR) division 64, approximately between 1300 and 2500 nanometers.

Although the non-inoculated and inoculated waveform 56 and 58, respectively, follow similar general patterns, the present inventors have recognized that they in fact differ at select wavelengths based on disease states. As a result, such differences can be distinguished in predetermined groups or patterns of spectral values for reliably detecting disease states.

Referring now to FIG. 4, an exemplar plot of a group 70 of spectral values 72 calculated in a "heat map" is provided in accordance with an aspect of the invention. The spectral values 72 are derived from the spectrum of electromagnetic radiation, such as from a waveform of FIG. 3, at a particular sampling time. Each spectral value 72 can quantify a relative difference between reflections (ρ) at differing wavelengths ($\lambda_i$, $\lambda_j$) between the lower and upper wavelengths 52 and 54, respectively. Accordingly, each spectral value 72 can emphasize distinctions between the differing wavelengths, certain ones of which being suitable for detection of stages of infection at particular times.

In one aspect, the spectral values 72 can be Normalized Differential Spectral Index (NDSI) values. Such NDSI values can be calculated as a difference between spectral reflections at first and second wavelengths (or bands) λi and $\lambda_j$, divided by a sum of the spectral reflections at the first and second wavelengths (or bands) λi and $\lambda_j$, respectively, such as according to the equation:

$$NDSI = \frac{\text{band}_i - \text{band}_j}{\text{band}_i + \text{band}_j}$$

Referring now to FIG. 5, in accordance with an aspect of the invention, for detection of disease in plants, the processor 20 can execute a process 73 to calculate multiple predetermined groups 70 or patterns of spectral values 72 from reflections of electromagnetic radiation from a plant 30 under study. Each group 70 includes spectral values 72 optimized to most characterize a particular stage of infection of disease for its group when compared to other stages. Accordingly, each group 70 can correspond to a likelihood of presence of that particular stage of infection. In one aspect, for *P. infestans* in potato or tomato, following a detection of electromagnetic radiation from a plant 30, the processor 20 can execute to calculate: a first group 70*a* of spectral values 72 optimized for detection of early infection ("Stage 1"); a second group 70*b* of spectral values 72 optimized for detection of biotrophic growth ("Stage 2"); a third group 70*c* of spectral values 72 optimized for detection of transition to necrotrophy ("Stage 3"); a fourth group 70*d* of spectral values 72 optimized for detection of necrotrophic lesion formation ("Stage 4"); a fifth group 70*e* of spectral values 72 optimized for detection of sporulation ("Stage 5"); and a sixth group 70*f* of spectral values 72 optimized for detection of disease-induced leaf death ("Stage 6").

With additional reference to FIG. 6A, a chart 80*a* indicates possible ranges 82*a* for spectral values 72 for indicating the various stages 84*a* of infection of *P. infestans* with varying percentages of accuracy 86*a*. As shown, spectral values 72 for detection of early infection ("Stage 1") could be optimized in the first group 70*a* by using reflections at wavelengths in only the SWIR division of the IR spectrum; spectral values 72 for detection of biotrophic growth ("Stage 2") could be optimized in the second group 70*b* by using reflections at wavelengths in only the NIR division of the IR spectrum; spectral values 72 for detection of transition to necrotrophy ("Stage 3") could be optimized in the third group 70*c* by using reflections at wavelengths in the SWIR and NIR divisions of the IR spectrum; spectral values 72 for detection of necrotrophic lesion formation ("Stage 4") could be optimized in the fourth group 70*d* by using reflections at wavelengths in the SWIR and NIR divisions of the IR spectrum; spectral values 72 for detection of sporulation ("Stage 5") could be optimized in the fifth group 70*e* by using reflections at wavelengths in only the SWIR division of the IR spectrum; spectral values 72 for detection of disease-induced leaf death ("Stage 6") could be optimized in the sixth group 70*f* by using reflections at wavelengths in the visible spectrum and SWIR division of the IR spectrum.

By way of example, the inventors have found that spectral values 72 for detection of early infection ("Stage 1"), at about 24 hours post inoculation, could be optimized in the first group 70*a* by using NDSI values based on any of the following combinations of wavelengths (formatted as X_first_wavelength, second_wavelength, in nanometers, where the NDSI value is calculated by subtracting the reflectance at the second wavelength from the reflectance at the first wavelength over the sum of the two reflectance at the specified wavelengths) (corresponding classification accuracies for each combination, derived from 500 iterations of a 70-30 training-testing dataset split, are also provided):

a. X2034.2029+X2031.2030—about 78% accuracy;

b. X2032.2029+X2032.2031+X2031.2029+X897.887+ X2032.2030+X2033.2029+X1948.1944+X827.826+ X2034.2029—about 74% accuracy;
c. X2032.2029+X2032.2031+X2031.2029+X897.887+ X2032.2030+X2033.2029+X1948.1944+X827.826— about 75% accuracy;
d. X2032.2029+X2032.2031+X2031.2029+X897.887+ X2032.2030+X2033.2029+X1948.1944—about 72% accuracy;
e. X2032.20294- X2032.2031+X2031.2029+X897.887+ X2032.2030+X2033.2029+X827.826+X2034.2029+ X2031.2030—about78% accuracy.

Spectral values 72 for detection of biotrophic growth ("Stage 2"), at about 36 to 60 hours post inoculation, could be optimized in the second group 70b by using NDSI values based on any of the following combinations of wavelengths:
a. X1874.1414+X1874.1415+X1874.1416+ X1137.973.1+X1136.973.1+X1138.966+X1138.965+ X1084.1080+X557.556—about 75% accuracy;
b. X1874.1414+X1874.1415+X1874.1416—about 66% accuracy;
c. X1137.973.1+X1136.973.1+X1138.966+X1138.965+ X1084.1080 about 67% accuracy;
d. X557.556—about 67% accuracy.

Spectral values 72 for detection of transition to necrotrophy ("Stage 3"), at about 84 hours post inoculation, could be optimized in the third group 70c by using NDSI values based on the following combination of wavelengths:
a. X970.962, X920.918, X1927.1922, X926.918, X1130.1015—about 89% accuracy.

Spectral value 72 for detection of necrotrophic lesion formation ("Stage 4"), at about 108 hours post inoculation, could be optimized in the fourth group 70d by using an NDSI value based on the following wavelengths:
a. X1982.1899—about 90% accuracy.

Spectral values 72 for detection of sporulation ("Stage 5"), at about 132 hours post inoculation, could be optimized in the fifth group 70e by using NDSI values based on any of the following combinations of wavelengths:
a. X2284.2276+X2285.2276+X1931.1919+X1931.1925 about 80%
b. X1932.1919+X1932.1920+X2286.2276—about 76% accuracy;
c. X2284.2276+X2285.2276+X2286.2276—about 71% accuracy;
d. X2284.2276+X2285.2276+X1931.1919—about 78% accuracy;
e. X2284.2276+X2285.2276+X1931.1919+X1931.1925+ X1931.1920 about 79% accuracy;
f. X2284.2276+X2285.2276+X1931.1919+X1931.1925+ X1931.1920+X1932.1919+X1932.1920—about 78% accuracy;
g. X2284.2276+X2285.2276+X1931.1922—about 78% accuracy;
h. X2284.2276—about 74% accuracy.

Spectral values 72 for detection of disease-induced leaf death ("Stage 6"), at about 24 hours post inoculation, could be optimized in the sixth group 70f by using NDSI values based on any of the following combinations of wavelengths:
a. X2284.2276, X1931.1922, X564.528—about 78% accuracy;
b. X2284.2276—about 70% accuracy;
c. X2284.2276+X1931.1922+X1932.1922+X558.5521+ X564.527+X560.533+X559.533+X561.533—about 80% accuracy;
d. X2284.2276+X2285.2276+X1931.1922+ X1932.1922+X564.528—about 79%
e. X2284.2276+X564.528—about 78% accuracy.

Preferably, a group 70 would include between two to ten spectral values 72.

Figure 5:
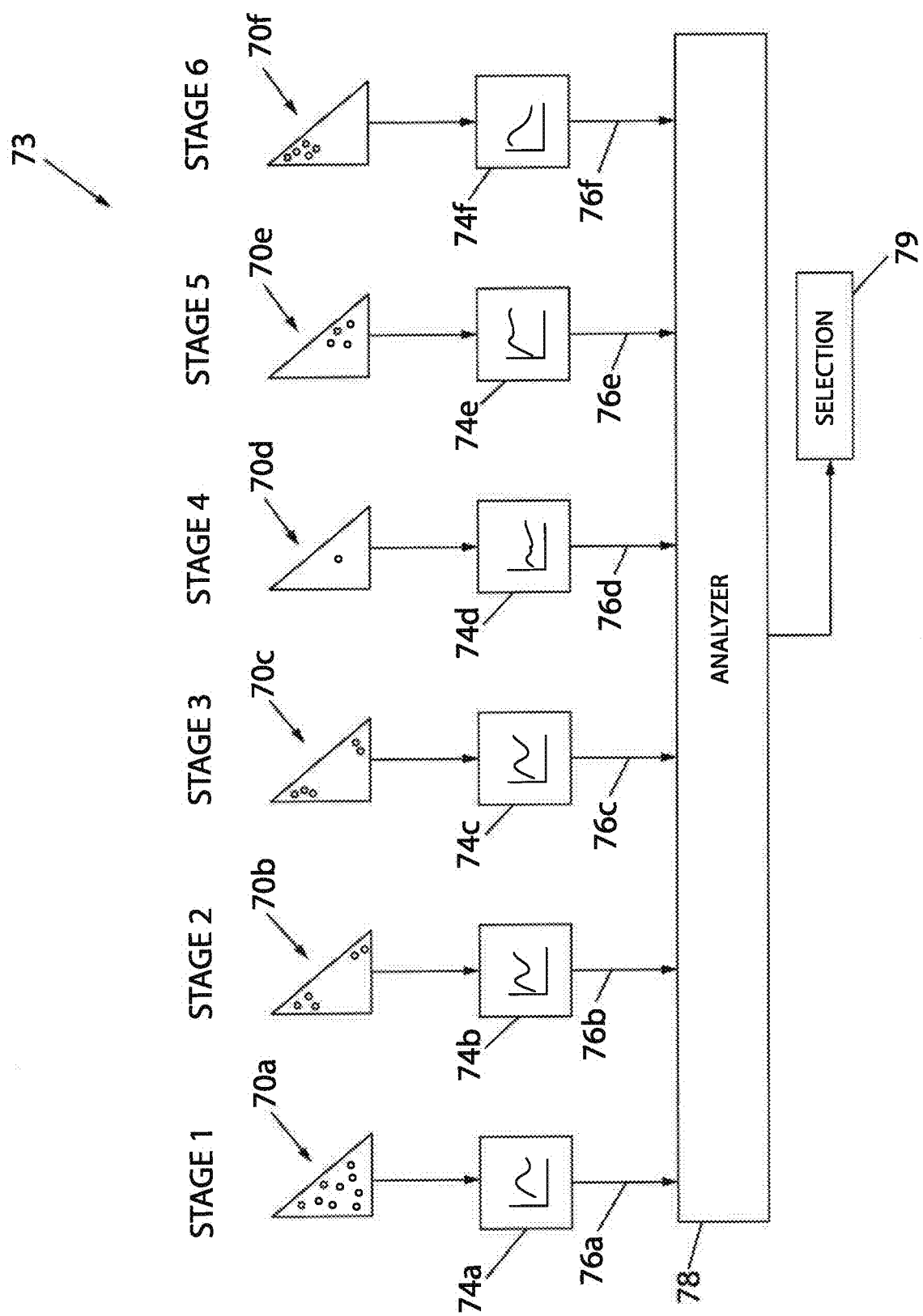
FIG. 5 is a process which can be executed by the system of FIG. 1 for applying spectral values as variables in models indicating stages of infection of disease to produce in accordance with an aspect of the invention.

Referring again to FIG. 5, the processor 20 can further execute the process 73 to apply the multiple groups 70 of spectral values 72 as variables in models 74 for indicating stages of infection of disease to produce outputs 76 indicating likelihoods of presence of the respective stages of infection in the plant. Each model 74 can execute a multivariate logistic regression using particular spectral values 72 to produce a probability for providing the output 76. Each model 74 could execute simultaneously or sequentially. The output 76 could be expressed as probability or percent likelihood of presence of the particular stage of disease. For *P. infestans* in potato or tomato, the first group 70a of spectral values 72 ("Stage 1") can be applied in a model 74a to produce an output 76a indicating a likelihood of presence of early infection; the second group 70b of spectral values 72 ("Stage 2") can be applied in a model 74b to produce an output 76b indicating a likelihood of presence of biotrophic growth; the third group 70c of spectral values 72 ("Stage 3") can be applied in a model 74c to produce an output 76c indicating a likelihood of presence of transition to necrotrophy; the fourth group 70d of spectral values 72 ("Stage 4") can be applied in a model 74d to produce an output 76d indicating a likelihood of presence of necrotrophic lesion formation; the fifth group 70e of spectral values 72 ("Stage 5") can be applied in a model 74e to produce an output 76e indicating a likelihood of presence of sporulation; and the sixth group 70f of spectral values 72 ("Stage 6") can be applied in a model 74f to produce an output 76f indicating a likelihood of presence of disease-induced leaf death.

In one aspect, the outputs 76 could be collectively sent to the I/O interface 18 for graphic display to a user. The user could then interpret the results to determine presence or absence of disease, and moreover, a stage of infection of the disease, if present. However, in another aspect, each of the outputs 76 could be sent to an analyzer 78 for producing a selection 79 indicating presence or absence of disease, and moreover, stage of infection of the disease, if present. The analyzer 78 could be a program executing to reference a library comprising historical test results and apply statistical analysis and/or machine learning to produce the selection 79. The selection 79, in turn, could be sent to the I/O interface 18 for graphic display to the user to provide a simplified result.

Figure 7:
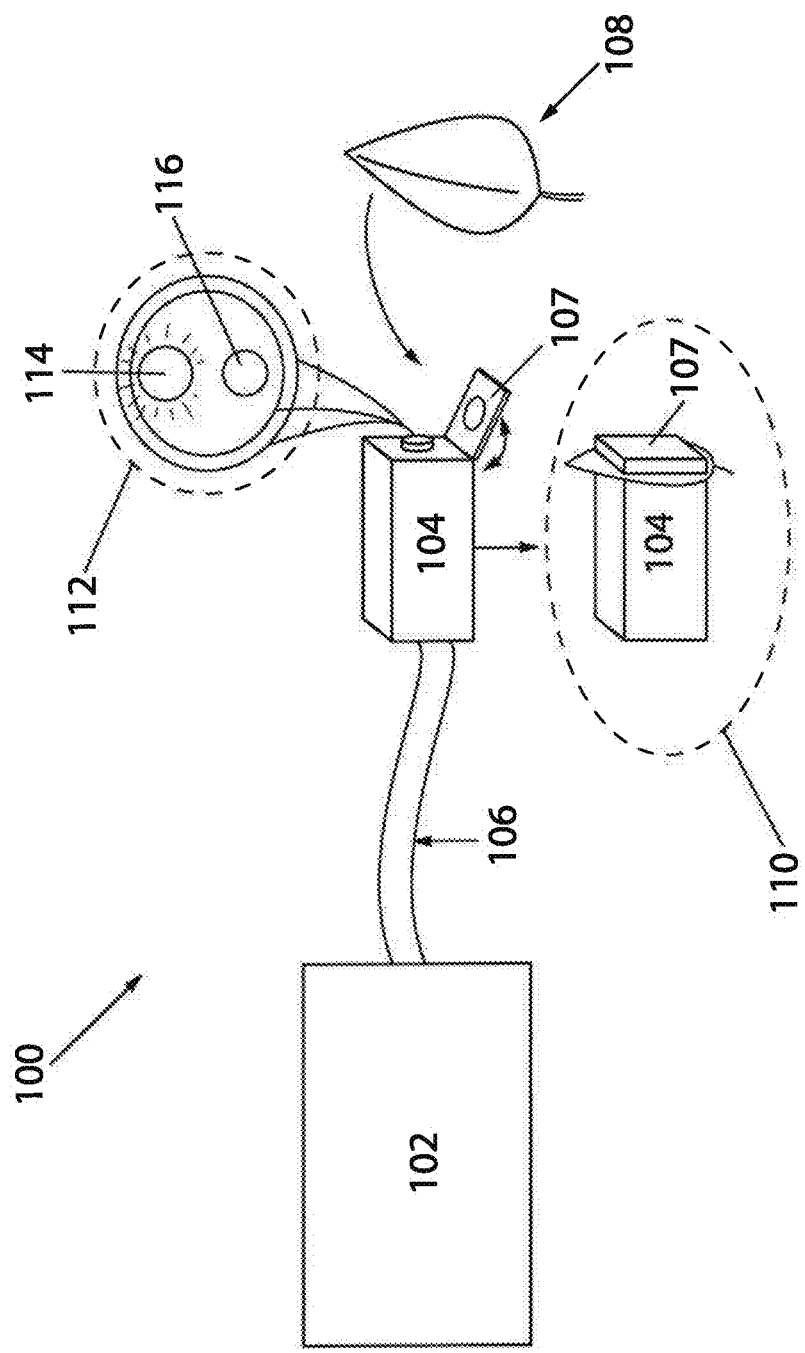
Figure 8:
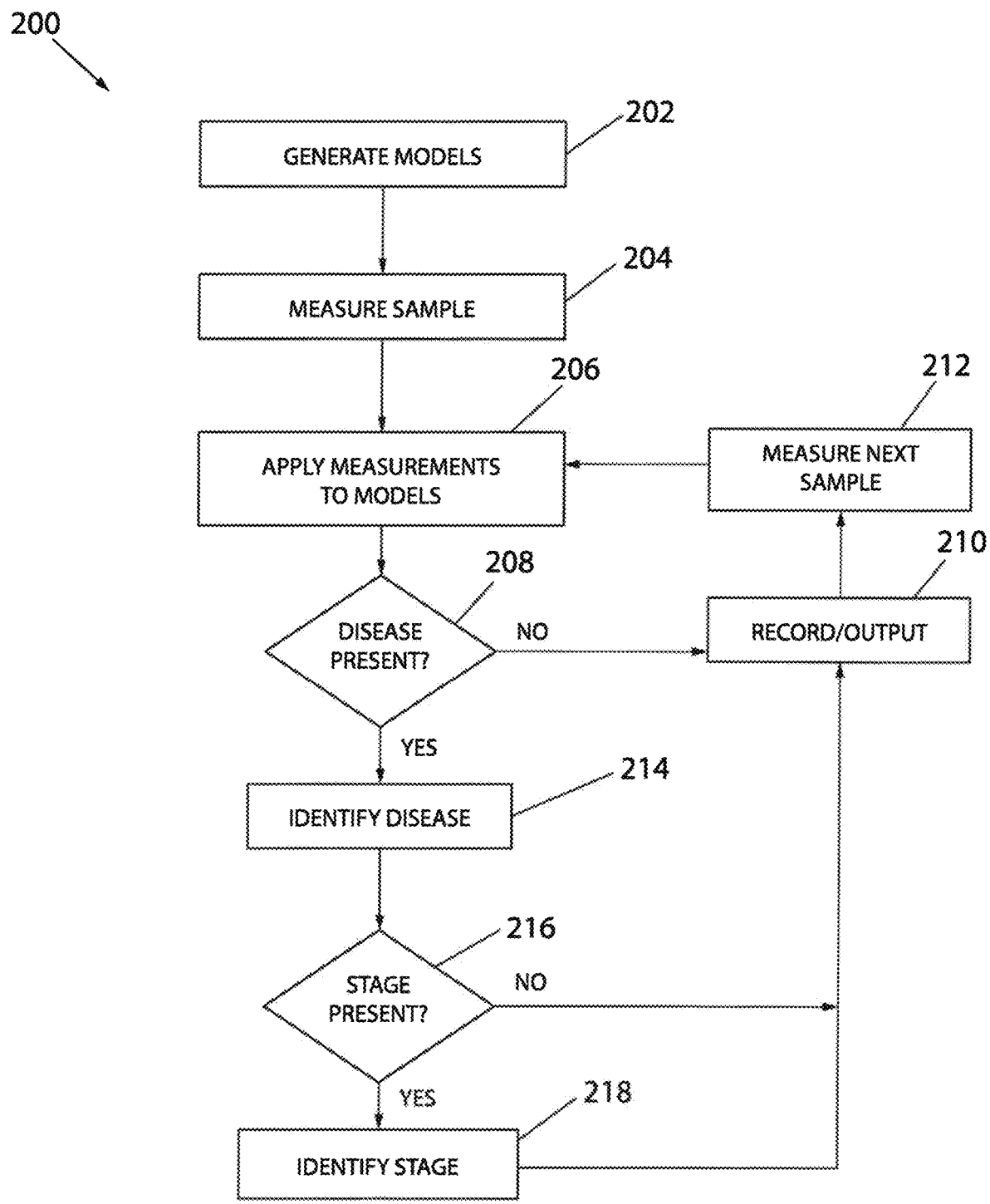
Figure 9:
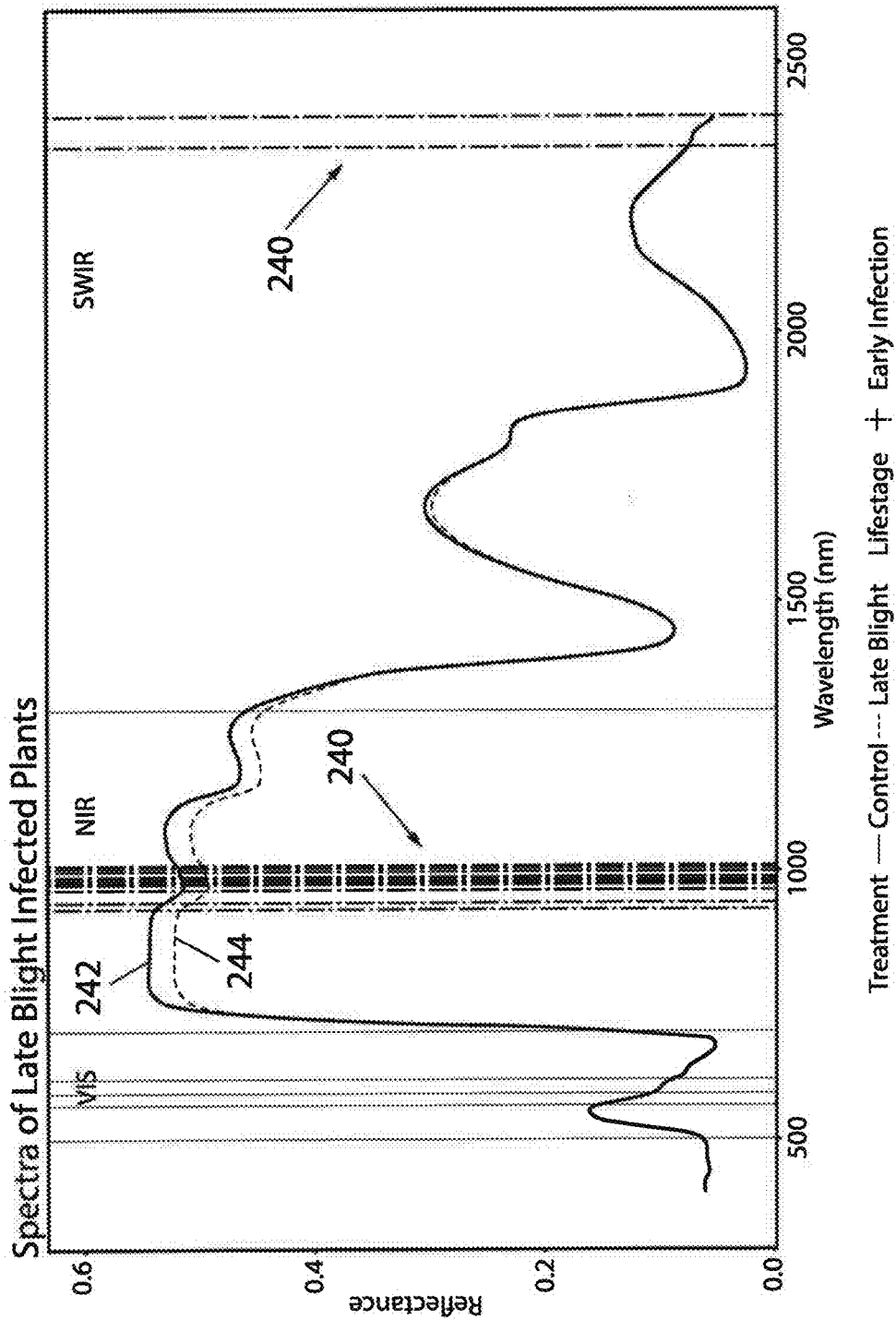
Figure 10:
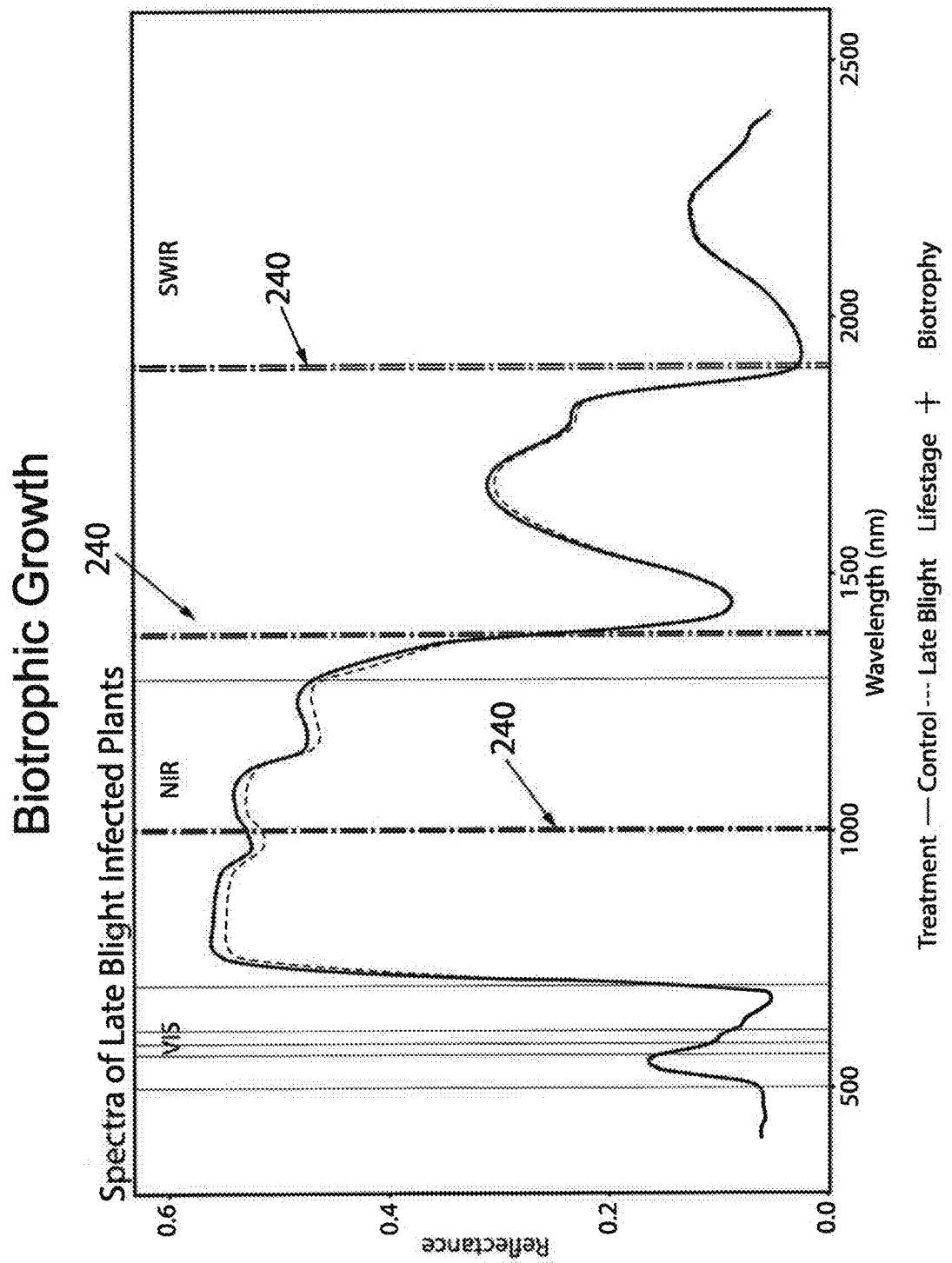
Figure 11:
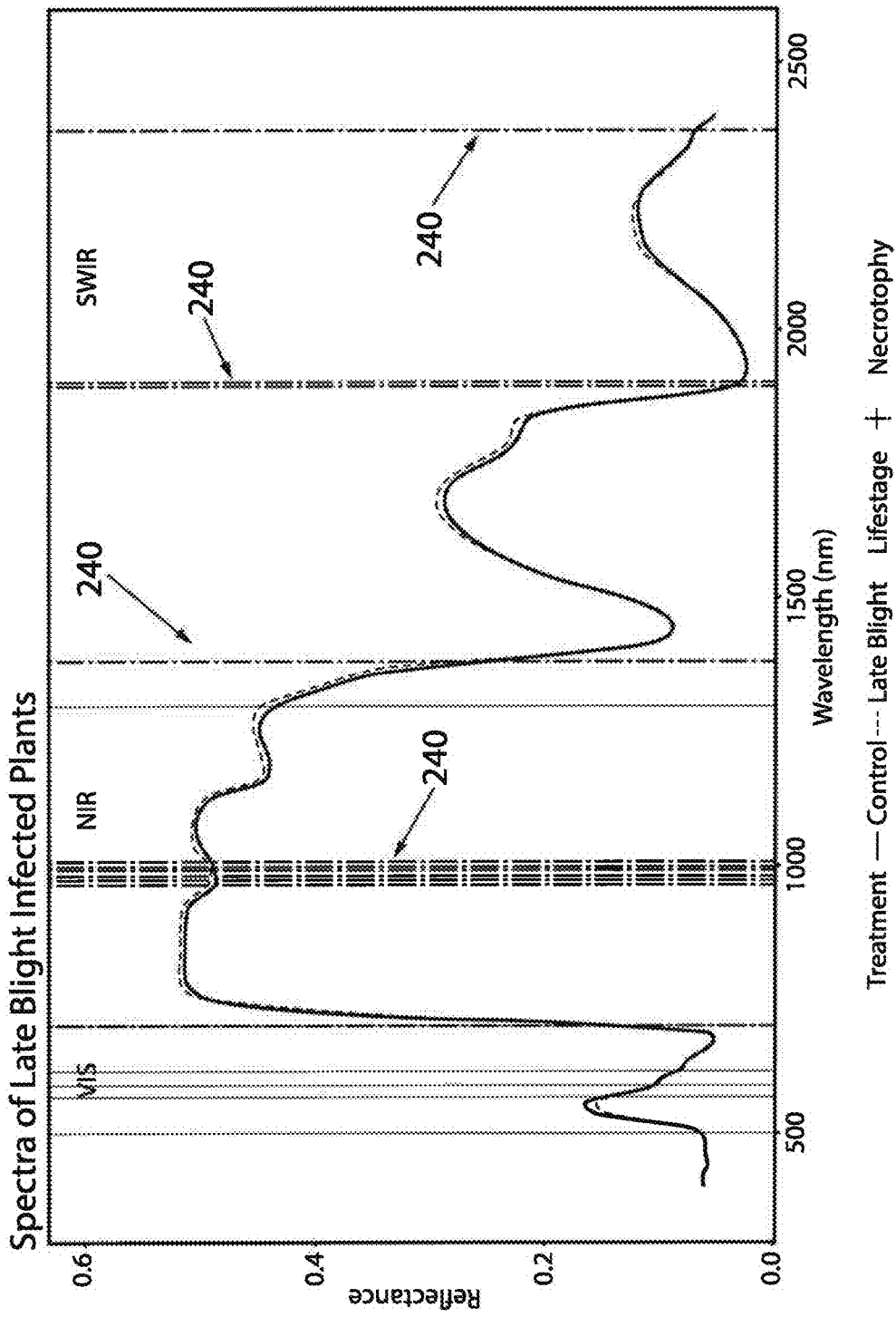
Figure 12:
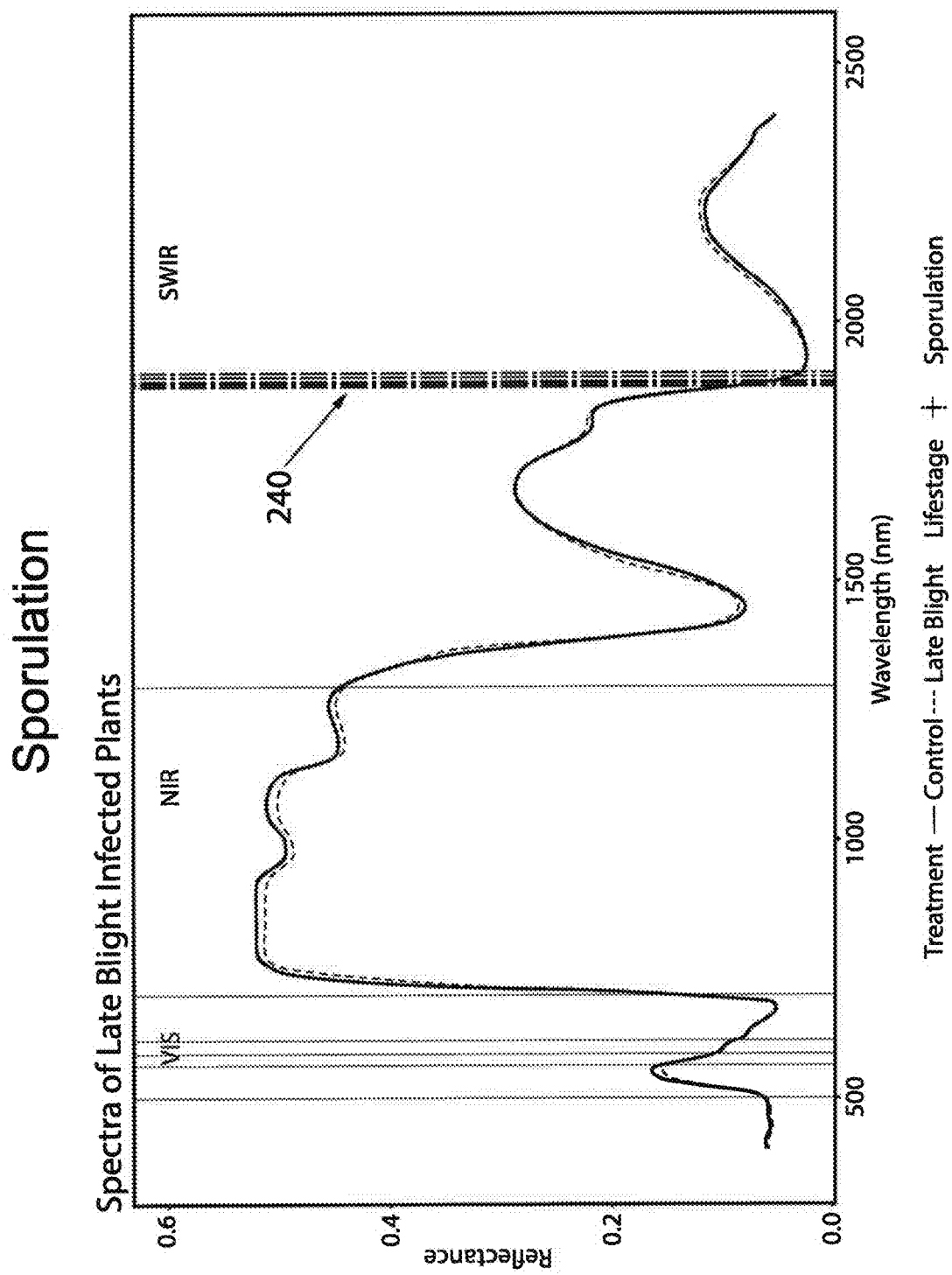
Figure 13:
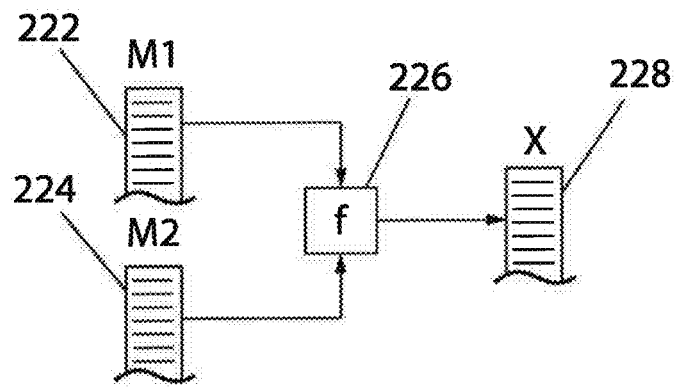

Referring now to FIG. 7, an alternative system 100 can be provided for detection of disease in plants in accordance with an aspect of the invention. The system 100 can include a combined control system 102, including a processor, data store, spectrometer and/or I/O interface, in communication with an enclosure 104, through a cable 106 providing I/O control and/or a waveguide. The enclosure 104 can include a door 107 having a clip or other mechanism for retaining a plant material 108, such as a leaf, under study. The plant material 108 can be held by the clip and, as shown in detail view I/O, the door 107 can be closed to contain at east a portion of the plant material 108 inside the enclosure 104 for testing.

With the plant material 108 held inside the enclosure 104 and the door 107 closed, the control system 102 can be triggered to initiate testing. When initiated, as shown in detail view 112, the control system 102 can trigger the enclosure 104 to project a spectrum of electromagnetic radiation, directed toward the plant material 108, from a radiating source 114, preferably including visible and infrared spectra. A lens 116 could then direct reflections from the plant material 108 to the spectrometer. The control system 102, with results from the spectrometer, can then calculate the predetermined groups 70 of spectral values 72, and apply the groups 70 of spectral values 72 as variables in a model 74 to produce outputs 76 indicating likelihoods of presence of stages of infection in the plant material 108 and/or the selection 79 for graphic display.

Figure 6A:
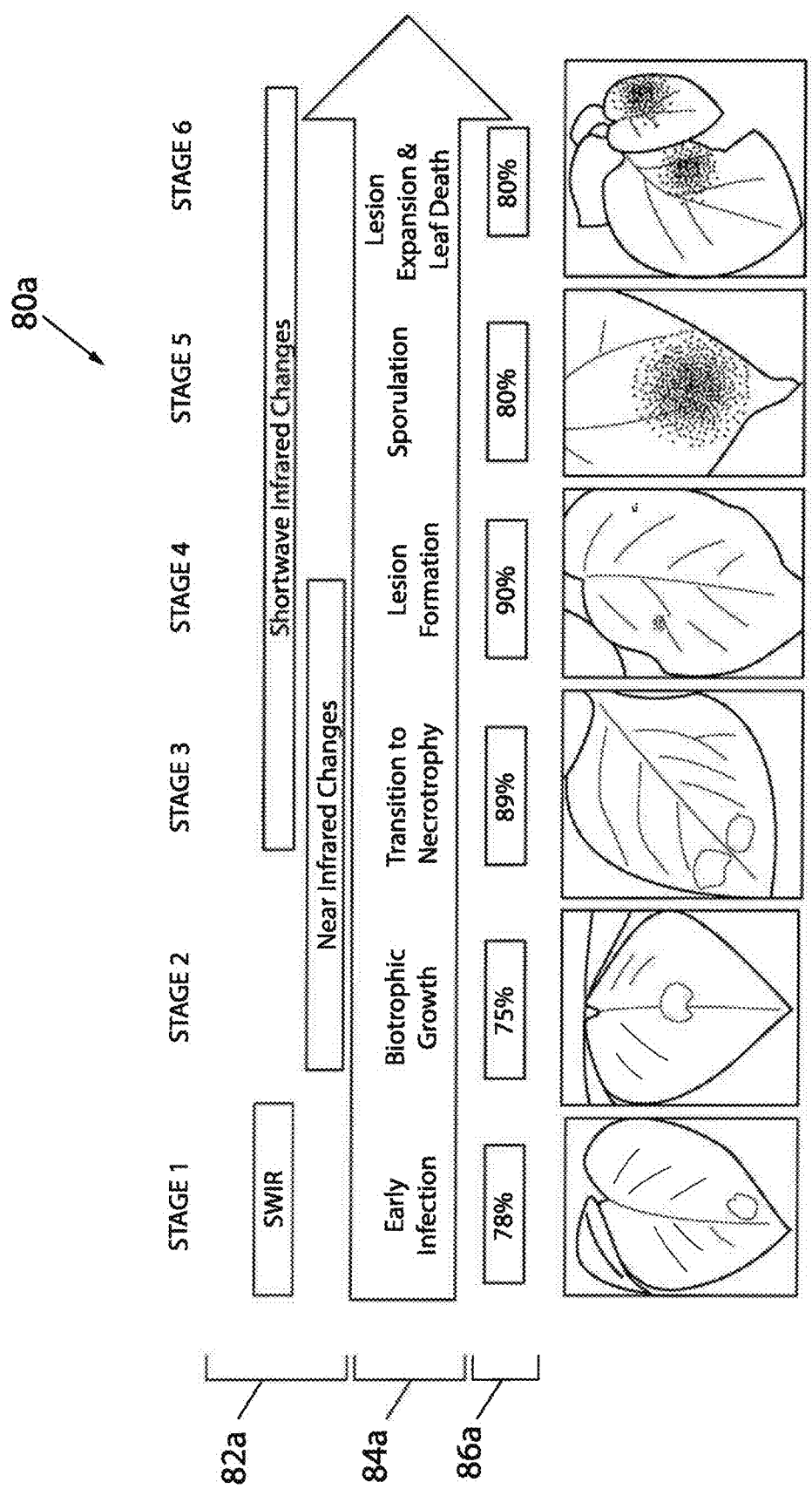
FIG. 6A is a chart indicating possible ranges for spectral values for indicating various stages of infection of *P. infestans* with varying percentages of accuracy in accordance with an aspect of the invention.
Figure 6B:
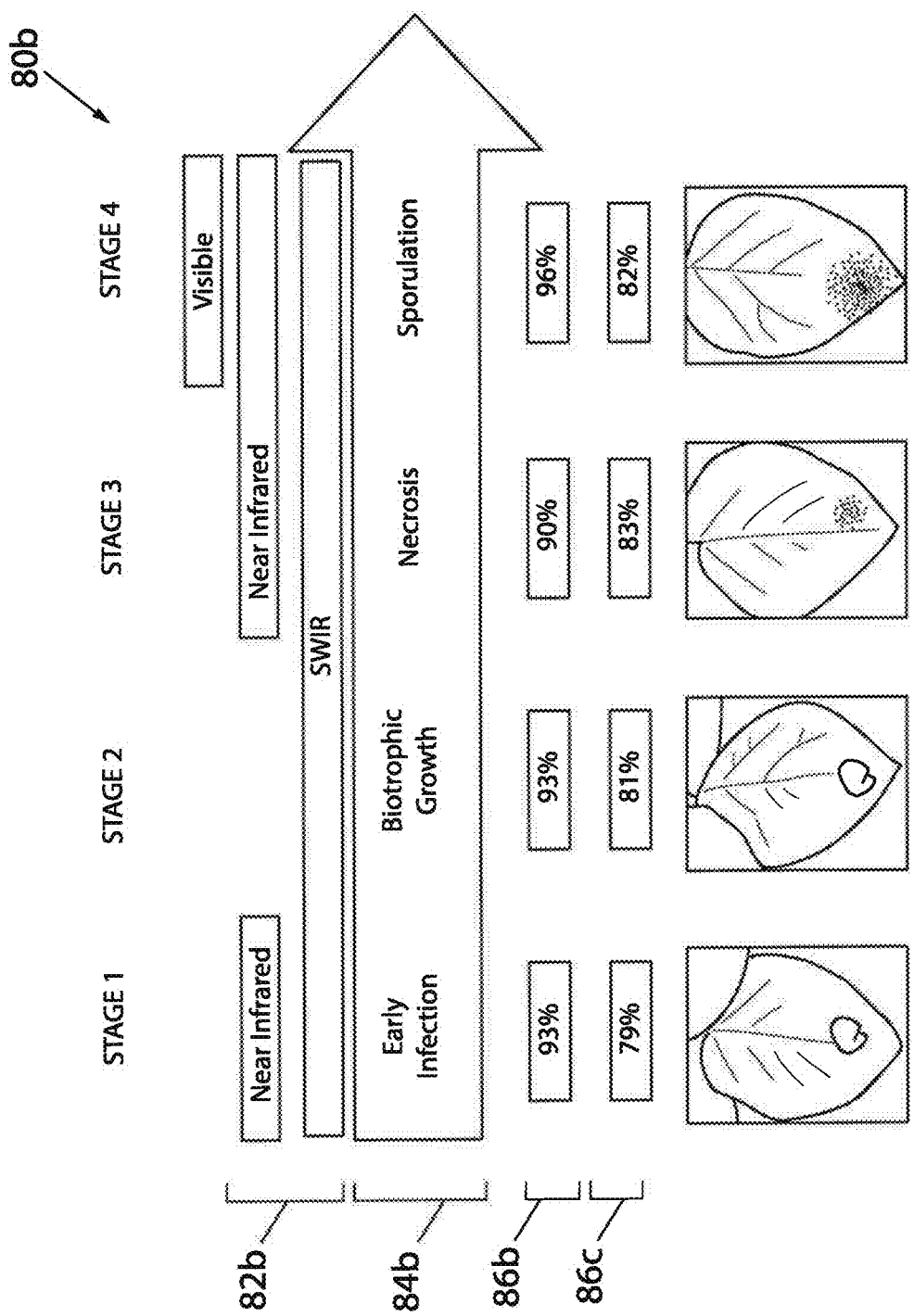
FIG. 6B is a chart indicating possible ranges for spectral values for indicating a fewer number of stages of infection of *P. infestans* with varying percentages of accuracy in alternative modes of detection in accordance with another aspect of the invention;

Referring now to FIG. 6B, in another aspect of the invention, a chart 80b indicates possible ranges 82b for spectral values 72 for indicating the various stages 84b of infection of *P. infestans* with varying percentages of accuracy 86b. In this aspect, a fewer number of stages 84b can be detected, in this case four, with different percentages of accuracy for each stage by using different NDSI values, similarly as described above with respect to FIG. 5.

In addition, in an alternative aspect of the invention, the fewer number of stages 84*b* can be detected, with varying percentages of accuracy 86*c*, using an application of coefficients as described herein. Referring now to FIG. 8, in such a system, the processor 20 can execute the process 200 to obtain reflection measurements from the spectrometer 16 and apply such measurements as variables in a model configured to indicate a likelihood of presence or absence of a disease in a plant. Beginning at step 202, the process can begin by generating models used for determining plant healthiness, presence of disease, such as *P. infestans* (late blight) and/or *A. solani* (early blight), and/or presence of stages of infection of a disease. By way of example, with additional reference to FIGS. 9-12, waveforms are provided illustrating reflection measurements versus wavelengths for plants inoculated with optimally identifiable stages of infection of *P. infestans* as determined by the inventors, including early infection (FIG. 9), biotrophic growth (FIG. 10), necrotrophic lesion formation (FIG. 11), and sporulation (FIG. 12), each in comparison with a healthy or "control" plant. The models can be generated and re-generated with adjustments as often as desired.

With additional reference to FIG. 13, in one aspect, to generate a given model, first and second spectrums of electromagnetic radiation 222 and 224, respectively, can be detected by the spectrometer 16. Each spectrum can represent an array of reflection measurements corresponding to wavelengths between lower and upper wavelengths, such as between 400 and 2400 nanometers, in given increments, such as every 1 nanometer. For example, each spectrum could have a first reflection measurement at 400 nanometers, a second reflection measurement at 401 nanometers, a third reflection measurement at 402 nanometers, and so forth. The first spectrum 222 ("M1") can be a control or reference data set captured with respect to a healthy plant (such as control curve 242 of FIG. 9). However, the second spectrum 224 ("M2") can be a captured data set for a given disease or stage of infection being targeted by the model (such as inoculated curve 244 of FIG. 9). The first and second spectrums 222 and 224, respectively, can then be applied to a function 226 to produce an array of coefficients 228 ("X") or multiplier values corresponding to the wavelengths between the lower and upper wavelengths. The function 226 is applied to produce coefficients 228 that are configured to emphasize identification of the given disease or stage (exhibited by the second spectrum 224). That is, the coefficients are determined to maximize contributions of reflection measurements at particular wavelengths which are most indicative of the given disease or stage.

Referring again to FIGS. 9-12, wavelengths which may maximize contributions of reflection measurements for the various stage of *P. infestans* are identified by bands 240. By way of example, for identifying the early infection stage of *P. infestans*, a reflection measurement at 1000 nanometers may provide a greater predictor of presence of this stage of infection than a reflection measurement at 500 nanometers (see FIG. 9). As a result, a coefficient corresponding to 1000 nanometers can be emphasized by the function 226 by configuring a greater value coefficient at 1000 nanometers and a lesser value coefficient at 400 nanometers. In one aspect, the function 226 can apply a partial least squares discriminant analysis with respect to the first and second spectrums 222 and 224, respectively, to generate the coefficients 228.

With additional reference to FIG. 14, coefficients 228 can be prepared for each given disease or stage of disease being targeted by the process for analysis. For example, first coefficients 228*a* ("X1") can correspond to an *A. solani* model comparing the reference data set M1 captured with respect to a healthy plant to a data set M2 for a plant inoculated with *A. solani*; second coefficients 228*b* ("X2") can correspond to a first stage *P. infestans* model (early infection) comparing the reference data set M1 captured with respect to a healthy plant to a data set M2 for a plant inoculated with first stage *P. infestans*; third coefficients 228*c* ("X3") can correspond to a second stage *P. infestans* model (biotrophic growth) comparing the reference data set M1 captured with respect to a healthy plant to a data set M2 for a plant inoculated with second stage *P. infestans*; fourth coefficients 228*d* ("X4") can correspond to a third stage *P. infestans* model (necrotrophic lesion formation) comparing the reference data set M1 captured with respect to a healthy plant to a data set M2 for a plant inoculated with third stage *P. infestans*; fifth coefficients 228*e* ("X5") can correspond to a fourth stage *P. infestans* model (sporulation) comparing the reference data set M1 captured with respect to a healthy plant to a data set M2 for a plant inoculated with fourth stage *P. infestans*; and so forth. In addition, sixth coefficients 228*f* ("X6") can correspond to plant healthiness comparing the reference data set M1 captured with respect to a healthy plant to an inverse of one or more data sets M2 for a plant inoculated with a given disease or stage. Accordingly, such models can be configured to indicate a likelihood of presence of diseases and/or stages in a plant.

Referring back to FIG. 8, after generating the models, the process can continue to step 204 in which a given plant sample can be measured by the spectrometer 16. Referring also to FIG. 14, the plant can be measured to produce a sample spectrum 230 ("M0") representing an array of reflection measurements corresponding to wavelengths between the lower and upper wavelengths, in increments corresponding to the models, such as every 1 nanometer. Reflection measurements of the sample spectrum 230 can then be applied as variables for indicating a likelihood of presence of diseases and/or stages in the plant. In particular, at step 206, each reflection measurement of the sample spectrum 230 can be multiplied by a coefficient for a given wavelength, for each of the models produced. An analyzer 232, in turn, can receive the products of the sample spectrum 230 separately multiplied by each set of coefficients 228 in separate paths. With these calculated values, the analyzer 232 can analyze the results of each path to determine a likelihood or probability of a disease being present, an identification of the disease if present, and/or an identification of a stage of infection of a given disease if present. In one aspect, the analyzer 232 can apply stages of multivariate regression to produce an output.

Still referring to FIG. 8, at decision step 208, the process can determine a likelihood of presence of a disease. If a disease is not likely to be present ("No"), the process can proceed to step 210 to record and output the results, then step 212 to measure a next sample spectrum 230, and then step 206 again to apply the new reflection measurements as variables with respect to the one or more models. However, if a disease is likely to be present ("Yes"), the process can proceed to step 214 to identify the likelihood of disease to a given probability. Then, at decision step 216, the process can determine whether the identified disease is comprised of stages of infection. For example, P. infestans could be comprised of four identifiable stages of infection based on targeted models, such as early infection, biotrophic growth, necrotrophic lesion formation, and/or sporulation. However, A. solani might not be comprised of any further identifiable stage of infection, aside from the disease itself. If the identified disease is not comprised of stages of infection ("No"), the process can proceed to step 210 to record and output the results of the disease itself, then step 212 to measure a next sample spectrum 230, and then step 206 to apply the new reflection measurements as variables again with respect to the one or more models. However, if the identified disease is comprised of multiple stages of infection ("Yes"), the process can proceed to step 218 to identify the stage of infection to a given probability. Then, the process can proceed to step 210 to record and output the results of the disease and stage, then step 212 to measure a next sample spectrum 230, and then step 206 to apply the new reflection measurements as variables again with respect to the one or more models.

Figure 14:
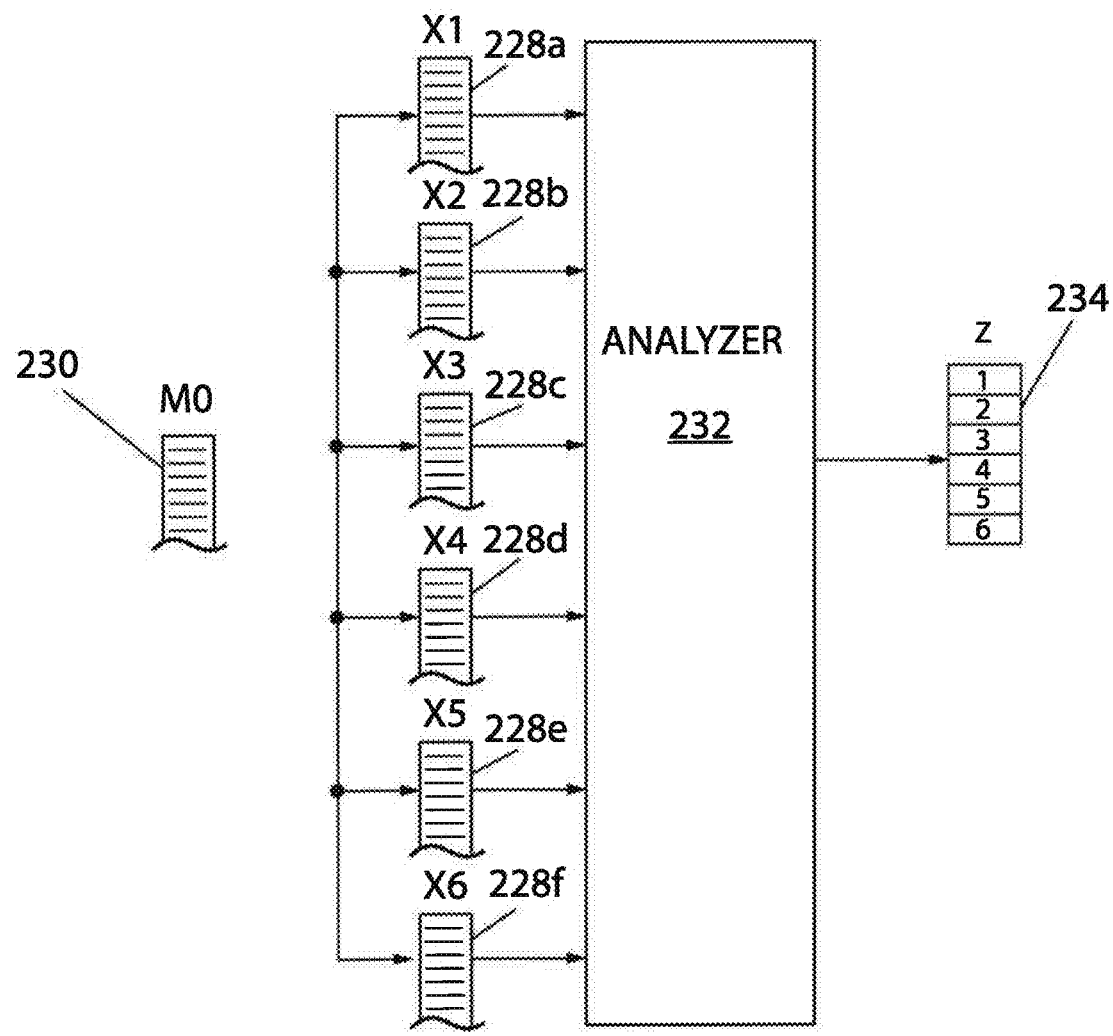

Referring again to FIG. 14, in one aspect, output 234 from the analyzer 232 could comprise a ranking ("Z") of the likelihood of presence of each disease and/or stage of infection of disease with probabilities, corresponding to the paths produced by the different models of coefficients 228. For example, when analyzing a sample spectrum 230 with respect to six different models X1-X6, the results of each can be ranked from most probable to least probable. Moreover, in some aspects, the first ranked result can be provided to an output, such as a graphic display implemented on a computer screen or mobile device.

Figure 15:
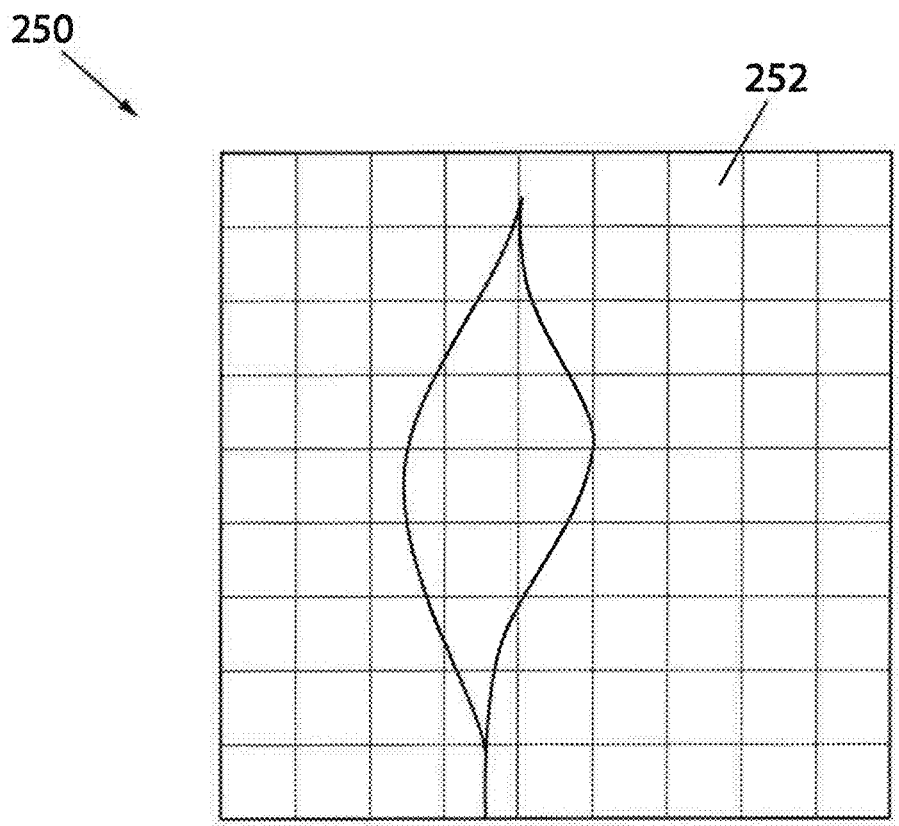

Referring now to FIG. 15, in another aspect of the invention, a spectroscopic imager can be used to capture images 250 comprising spectral pixels 252 in which each spectral pixel comprises reflection measurements corresponding to wavelengths in a spectrum. For example, an imager can capture the image 250 of a plant leaf comprising in rows and columns of spectral pixels 252. Each spectral pixel can comprise an individual sample spectrum M0, like the sample spectrum 230, which could be modeled and analyzed in the system of FIG. 14. Depending on distance from the plant being measured, and resolution of the imager, greater or lesser numbers of sample spectrums M0, covering greater or lesser areas of plants, can be captured and analyzed in varying degrees. Accordingly, such analysis can be carried on a micro level, such as with respect to leaves and plants, and/or on a macro level, such as with respect to fields and terrains.

Figure 16:
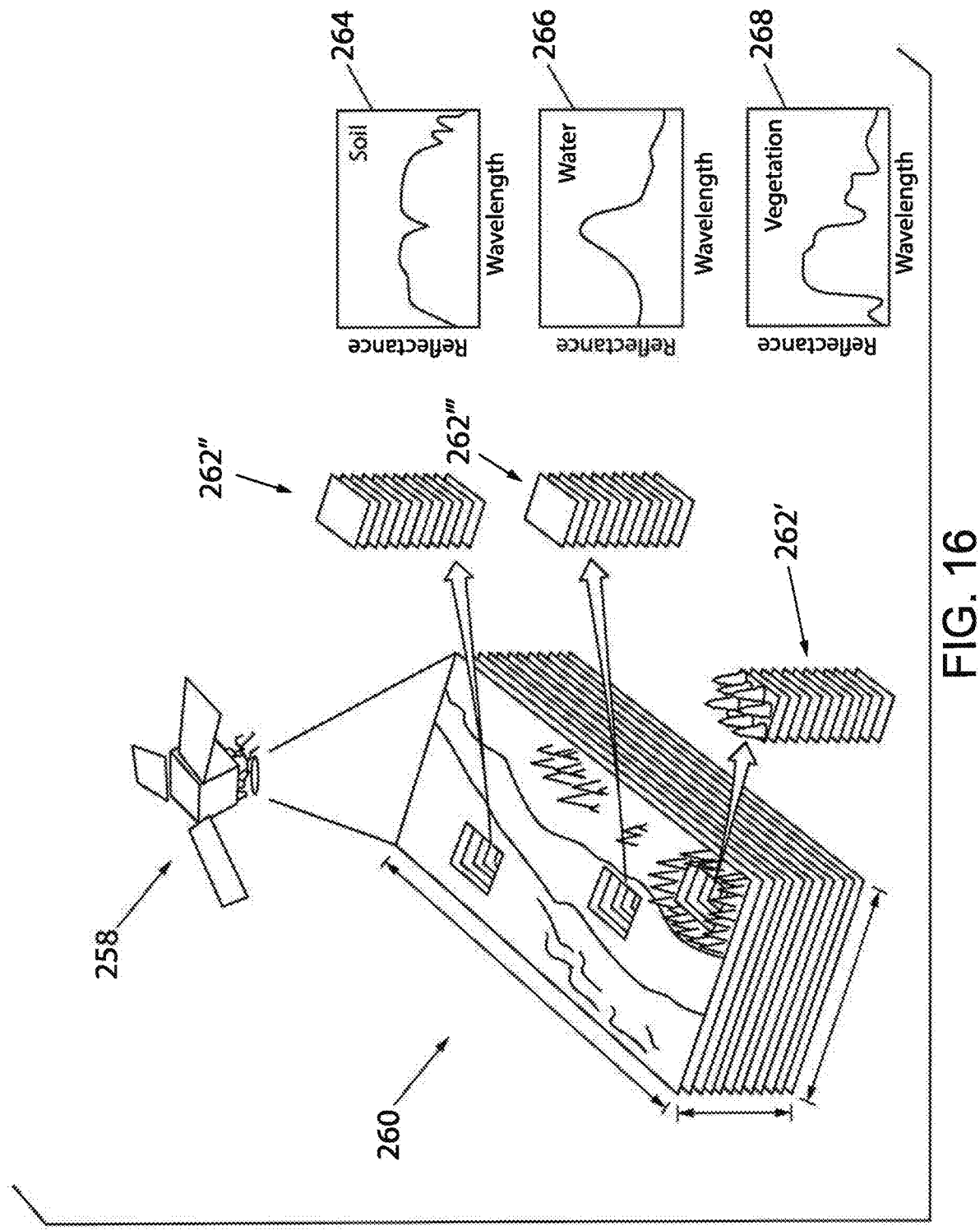

With additional reference to FIG. 16, in one aspect, an overhead vehicle 258, such as an aircraft, drone or satellite, could include such an imager used to capture images 260 of a large terrain, such as swath of the Earth's surface, in which spectral pixels 262 of the image each comprise reflection measurements corresponding to wavelengths in a spectrum. At this macro level, an image 260 could capture large areas of plants and vegetation, such as a first spectral pixel 262' capturing densely populated frees. However, the image 260 could also capture significant areas of non-plant material, such as a second spectral pixel 262" capturing soil, and a third spectral pixel 262'" capturing water. Prior to analyzing any spectrum associated with a pixel, the processor 20 could execute a filter to remove certain non-plant spectral pixels, such as the second and third spectral pixels 262" and 262'", respectively, which do not correspond to plant material like the first spectral pixel 262'. In one aspect, such a system can efficiently determine reflection measurement waveforms of the second spectral pixels 262" as corresponding to a stored soil waveform 264, and reflection measurement waveforms of the third spectral pixels 262'" as corresponding to a stored water waveform 266, and filter such spectral pixels from analysis based on their matched similarities. Also, the system can efficiently determine reflection measurement waveforms of the third spectral pixels 262'" as corresponding to a stored vegetation waveform 268 and being processing of such pixels for spectral analysis for determining likelihood of presence of diseases and/or stages of infection.

Certain terminology is used herein for purposes of reference only, and thus is not intended to be limiting. For example, terms such as "upper," "lower," "above," and "below" refer to directions in the drawings to which reference is made. Tennis such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor" can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and/or can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as coming within the scope of the following claims. All of the publications described herein including patents and non-patent publications are hereby incorporated herein by reference in their entireties.

What is claimed is:

1. A system for detection of disease in plants, comprising:
a spectrometer configured to detect a spectrum of electromagnetic radiation reflected from a plant at a plurality of wavelengths, the spectrum comprising reflection measurements corresponding to wavelengths; and
a processor executing a program stored in a non-transient medium to apply the reflection measurements as variables in a predetermined model configured to indicate a likelihood of presence of a disease in the plant and output the likelihood of presence of the disease in the plant;
wherein the model provides an array of coefficients multiplied by each reflection measurement, wherein each coefficient corresponds to a given wavelength and emphasizes identification of a disease or stage of infection of disease.

2. The system of claim 1, wherein the coefficients are determined by applying a partial least squares discriminant analysis with respect to first and second spectrums, the first spectrum comprising reflection measurements corresponding to wavelengths from a plant free from the disease or stage of infection of disease, and the second spectrum comprising reflection measurements corresponding to wavelengths from a plant having the disease or stage of infection of disease.

3. The system of claim 1, wherein the reflection measurements correspond to wavelengths between 400 and 2400 nanometers.

4. The system of claim 3, wherein the reflection measurements are provided in increments of at least 1 nanometer.

5. The system of claim 1, wherein the reflection measurements are applied to indicate a likelihood of presence of *Phytophthora infestans* (*P. infestans*) or *Alternaria solani* (*A. solani*).

6. The system of claim 1, wherein the reflection measurements are applied to indicate a likelihood of presence of one or more stages of infection of *P. infestans*.

7. The system of claim 6, wherein the stages of infection comprise:
early infection; biotrophic growth; necrotrophic lesion formation; and sporulation.

8. The system of claim 6, wherein the model produces an output ranking the likelihood of presence of each stage of infection.

9. The system of claim 1, wherein the reflection measurements are transformed into spectral values, each spectral value quantifying a relative difference between reflection measurements at differing wavelengths to emphasize identification of the disease.

10. The system of claim 9, wherein the spectral values are Normalized Differential Spectral Index (NDSI) values, each NDSI value being calculated as a difference between reflection measurements at differing wavelengths divided by a sum of the reflection measurements at the differing wavelengths.

11. The system of claim 10, wherein the model applies no more than ten NDSI values for indicating the likelihood of presence of the disease or stage of infection of disease.

12. The system of claim 1, wherein the processor further executes to send the likelihood of presence of the disease or stage of infection of disease to a graphic display.

13. The system of claim 1, wherein the spectrometer is attached to a contact probe, an agricultural implement or an aerial vehicle.

14. A system for detection of disease in plants, comprising:
an imager configured to a capture an image comprising a plurality of spectral pixels, each spectral pixel corresponding to a spectrum of electromagnetic radiation reflected at a plurality of wavelengths, the spectrum comprising reflection measurements corresponding to wavelengths; and
a processor executing a program stored in a non-transient medium to apply reflection measurements at each spectral pixel as variables in a predetermined model configured to indicate a likelihood of presence of a disease of a plant at the spectral pixel and output the likelihood of presence of the disease in the plant
wherein the model provides an array of coefficients multiplied by each reflection measurement, wherein each coefficient corresponds to a given wavelength and emphasizes identification of a disease or stage of infection of disease.

15. The system of claim 14, wherein the coefficients are determined by applying a partial least squares discriminant analysis with respect to first and second spectrums, the first spectrum comprising reflection measurements corresponding to wavelengths from a plant free from the disease or stage of infection of disease, and the second spectrum comprising reflection measurements corresponding to wavelengths from a plant having the disease or stage of infection of disease.

16. The system of claim 14, wherein the reflection measurements correspond to wavelengths between 400 and 2400 nanometers.

17. The system of claim 14, wherein the reflection measurements are transformed into spectral values, each spectral value quantifying a relative difference between reflection measurements at differing wavelengths to emphasize identification of the disease.

18. The system of claim 14, wherein the processor further executes a filter to remove spectral pixels which do not correspond to plants.

* * * * *